US012718913B2

(12) United States Patent
De Magalhaes et al.

(10) Patent No.: US 12,718,913 B2
(45) Date of Patent: Aug. 25, 2026

(54) CONSOLIDATION AND PRIORITIZATION OF PATIENT CRITICAL NOTIFICATIONS

(71) Applicant: Roche Diagnostics Operations, Inc., Indianapolis, IN (US)

(72) Inventors: Chloe De Magalhaes, Barcelona (ES); Yasser Mohamed Reda Abdelgawad Ibrahim, Kassel (DE); José Carlos Pérez Pérez, Sabadell (ES)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 219 days.

(21) Appl. No.: 18/356,856

(22) Filed: Jul. 21, 2023

(65) Prior Publication Data

US 2024/0029841 A1 Jan. 25, 2024

(30) Foreign Application Priority Data

Jul. 25, 2022 (EP) .................................... 22382709

(51) Int. Cl.

| | |
|---|---|
| ***G16H 10/00*** | (2018.01) |
| ***G16H 10/40*** | (2018.01) |
| ***G16H 15/00*** | (2018.01) |
| ***G16H 40/20*** | (2018.01) |
| ***G16H 50/50*** | (2018.01) |

(52) U.S. Cl.

CPC ............ *G16H 10/40* (2018.01); *G16H 15/00* (2018.01); *G16H 40/20* (2018.01)

(58) Field of Classification Search

CPC ........ G16H 10/40; G16H 15/00; G16H 40/20; G16H 10/60; G16H 40/63

See application file for complete search history.

(56) References Cited

U.S. PATENT DOCUMENTS

| | | | | |
|---|---|---|---|---|
| 11,545,241 | B1 * | 1/2023 | Holmes | ........... G06Q 10/06311 |
| 2007/0122783 | A1 | 5/2007 | Habashi | |
| 2009/0048870 | A1 | 2/2009 | Godshall et al. | |
| 2011/0106565 | A1 | 5/2011 | Compton et al. | |

(Continued)

FOREIGN PATENT DOCUMENTS

| | | | |
|---|---|---|---|
| EP | 2416267 | A1 | 2/2012 |
| JP | 2007-057543 | A | 3/2007 |

(Continued)

OTHER PUBLICATIONS

European Search Report issued Jan. 3, 2023, in Application No. 22382709.8, 2 pp.

(Continued)

*Primary Examiner* — Maroun P Kanaan

(74) *Attorney, Agent, or Firm* — KATTEN MUCHIN ROSENMAN LLP

(57) ABSTRACT

A computer-implemented method of consolidating critical information for a patient in a laboratory is presented. The method comprises selecting a patient to monitor from a population of patients associated with the laboratory, extracting information for the patient from a plurality of laboratory sources in the laboratory, determining if the extracted patient information is critical to care of the patient, and outputting the extracted patient critical information to a single display dashboard for display to a laboratory operator.

22 Claims, 3 Drawing Sheets

(56) References Cited

U.S. PATENT DOCUMENTS

| | | | | |
|---|---|---|---|---|
| 2013/0110535 | A1 | 5/2013 | Eaton et al. | |
| 2015/0310176 | A1* | 10/2015 | Chen | H04L 51/214 705/2 |
| 2019/0156921 | A1* | 5/2019 | Kohli | G16H 10/20 |
| 2022/0084645 | A1* | 3/2022 | Ginsburg | G16H 10/60 |
| 2022/0230714 | A1* | 7/2022 | Batman | G16H 40/67 |

FOREIGN PATENT DOCUMENTS

| | | | |
|---|---|---|---|
| JP | 2011-090484 | A | 5/2011 |
| JP | 2012-073695 | A | 4/2012 |
| JP | 5542201 | B2 | 7/2014 |
| JP | 2016-021189 | A | 2/2016 |
| JP | 2016-528973 | A | 9/2016 |
| JP | 2019/102903 | A1 | 6/2019 |
| WO | 2015011592 | A2 | 1/2015 |

OTHER PUBLICATIONS

Notice of Reasons for Refusal issued Aug. 20, 2024, from Japanese Application No. 2023-120125, 8 sheets.

* cited by examiner

200

| 210 Work Flow Occurance | 215 | 225 Grading: Critical / Normal — Notification | 220, 227 Grading: Critical / Normal — Error | 230 Either Normal or STAT (Critical) order |
|---|---|---|---|---|
| Order/ tube received host/ manual | Time Lapse | X | | Set time over |
| | Error | | X | HCA Rejection Patient Exists (Action) |
| | Alarms | | X | Host Down |
| Sample seen Pre-Analyic | Time Lapse | X | | Sample seen message time lapse |
| | Error | | X | Mechanical Issue |
| | Alarms | X | | Instrument off |
| | Masking | X | | Instrument Masked |
| Sample seen Instrument | Time Lapse | X | | |
| | Error | | X | Barcode Error |
| | Alarms | | X | QC Alarm |
| | Masking | X | | |
| Results | Time Lapse | X | | |
| | Error | | X | VOR Result |
| | Alarms | | X | QC Alarm |
| | No Result | X | | ??? Received |
| Validation | Time Lapse | X | | |
| | Other | X | | Manual Validation |
| Send Results | Time Lapse | | X | |
| | Error | | X | Host Disconnect |

FIG. 3

CONSOLIDATION AND PRIORITIZATION OF PATIENT CRITICAL NOTIFICATIONS

CROSS-REFERENCE TO RELATED APPLICATIONS

This application claims priority to European Patent Application No. 22382709.8, filed Jul. 25, 2022, the disclosure of which is hereby incorporated by reference in its entirety.

TECHNICAL FIELD

The present disclosure generally relates to the consolidation and prioritization of patient critical notifications in a laboratory setting on a single dashboard display.

BACKGROUND

Current laboratory dashboard display solutions are typically overwhelmed with data due to the large amount of data-generating events that occur in a typical laboratory. This situation can create a problem related to prioritization of important information such as, for example, patient critical information. The important patient critical information can get lost to a laboratory operator in the sea of data created and displayed in a typical laboratory.

For example, typically, patient critical alarms related to a specific patient may need to be viewed on several different displays in the laboratory. Typically, a laboratory operator may have view two to four or more laboratory displays in order to track patient critical information for a specific patient. Additionally, when a laboratory operator needs to trace a patient critical alarm, the laboratory operator may need to view an additional three to four or more laboratory displays in order to the detect the source of the patient critical alarm, to receive details concerning the patient critical alarm, and to troubleshoot the patient critical alarm. Having to view all these different laboratory displays in order to find and resolve patient critical information can take valuable time and resources.

Document EP 2416267 A1 discloses a task aggregation system in a laboratory that can the tasks aggregated according to typology and order according to urgency. However, the tasks in this system are related to test samples, not patient specific notifications.

Document US Pub. 2011/0106565 A1 discloses providing proximity-based task lists to clinicians based on the location of clinicians with authorization and availability to complete the task and the task criteria.

Document US Pub. 2013/0110535 A1 discloses providing clinical information to clinicians based on the location of the clinician and the location of a patient experiencing a healthcare code so that the clinician nearest to the patient can respond quickly to the coding patient.

SUMMARY

It is an object of the present disclosure to consolidate and prioritize laboratory data according to patient criticality and patient impact and present the laboratory data quickly, clearly, and efficiently to a laboratory operator.

According to one aspect of the present disclosure, a computer-implemented method of consolidating critical information for a patient in a laboratory is presented.

The method comprises selecting a patient to monitor from a population of patients associated with the laboratory, wherein at least one sample from said patient was requested to be processed by a laboratory source comprised in said laboratory. Information for the patient from a plurality of laboratory sources in the laboratory is extracted by a laboratory control unit. The laboratory control unit is communicatively connected to the plurality of laboratory sources. The information for the patient comprises a test result obtained from processing said sample.

The laboratory control unit determines if the extracted patient information is critical to care of the patient, wherein said determining comprises determining if the test result indicates that the sample, laboratory source or test comprised errors, or if the test result was within or outside a normal test result range, or determining, from additional information relating to critical care, that the extracted patient information is critical to care of the patient, wherein said extracted patient critical information is critical to care if a test result is urgently required for life-saving treatment of the patient. The extracted patient critical information is, then, outputted by the laboratory control unit to a single display dashboard for display to a laboratory operator or a physician.

Information that may be critical to the patient can include, for example, issues with any laboratory workflow steps that can impede receiving test results for that patient in a timely manner or patient test results that can have an impact a patient's diagnosis or wellbeing.

Additional information that relates to critical care may be data relating to the patient that indicates that the result is urgently needed. Such data may, for example, include information that the patient is in an Intensive Care Unit, or previous test results indicating that the patient may suffer from a severe condition, such as a heart condition, or, in the case of a pregnant woman, high blood pressure as an indication for pre eclampsia, or symptoms that may indicate a sepsis. Such additional information may be obtained from any one or more laboratory sources.

The control unit would, in one embodiment, be configured to determine if the test result indicates that the patient is in a critical situation, or if the additional information indicates that the test result is urgently needed.

In a specific embodiment, the laboratory control unit determines that a test result is urgently needed if the test result indicates that the patient is in a critical situation, or information relating to the patient received by the laboratory control unit indicates that the patient is in a critical situation. As further described herein, a test result may indicate that the patient is in a critical situation if the test result is above or below certain thresholds. The information relating to the patient may be information as further described herein, which may, as one example, be information of the localization of the patient (e.g. the ICU).

In one embodiment, once the control unit has determined that the test result is urgently needed, the control unit is configured to create an alert which is sent to a display of a device where the laboratory operator is logged in, and wherein the alert overrides any other messages on the display.

Information that may be critical to the patient can include, for example, issues with any laboratory workflow steps that can impede receiving test results for that patient in a timely manner as well as any patient test results that can have an impact a patient's diagnosis or wellbeing. If such an issue is determined, the control unit may automatically reorder the test, or determine from information obtained from different connected laboratory sources a laboratory source that may be operable to process the sample, and route the sample to said laboratory source for processing and generating the test result.

The plurality of laboratory sources can comprise, for example, HCA (Host Connectivity Agent), laboratory databases, monitoring and validation processes, and/or ICA (Instrument Connectivity Agent).

The population of patients associated with the laboratory can be stored in a laboratory database communicatively connected to a laboratory control unit. In one embodiment, the population of patients can be extracted from the laboratory database by the laboratory control unit and displayed to a laboratory operator. In one embodiment, the laboratory operator can select a patient from the population of patients being displayed by using an input device connected to the laboratory control unit. The input device can be a keyboard, mouse, touchpad, touchscreen, and the like.

In one embodiment, the patient critical information can be stored in the laboratory database, which is communicatively connected to a laboratory control unit. This patient critical information can then be extracted from the laboratory database by the laboratory control unit. The laboratory control unit can be also communicatively connected to the plurality of laboratory sources in order to receive patient critical information from the plurality of laboratory sources as it occurs.

The computer-implemented method further comprises receiving laboratory workflow event information from the laboratory control unit when the patient critical information is the result of issue(s) with the laboratory workflow. In this embodiment, the laboratory workflow event information can also be displayed on the single display dashboard along with the patient critical information.

A laboratory workflow event may, in one embodiment, be an error occurring in a laboratory source, such as a pre-analytical device, a sample transport device (e.g. a conveyor connected to other physical laboratory sources), or an analytical device. The control unit would, in this embodiment, be configured to receive error information from such a laboratory source, connect the error information with the patient in the database, infer an action to be taken based on the patient critical information and display the patient critical information and the action on the screen of the operator.

Examples of such actions may be to automatically order a new test for processing the sample based on the current critical alarm, to repeat the test to obtain a confirmation of the result, or to alert a physician that the patient should be taken to an Intensive Care Unit.

The computer-implemented method further comprises receiving laboratory workflow event information from the laboratory control unit when a laboratory workflow event comprises a patient critical information such as, for example, a patient critical test result. In this embodiment, the laboratory workflow event information can be displayed on the display dashboard along with the patient critical information.

A patient critical test result may be a test result that lies outside of a defined threshold of a normal test result. For given tests, thresholds of normal test results are known and communicated to the user, e.g. in a package insert of the test reagents. A control unit, e.g. of a laboratory source capable of performing a given test, or the laboratory control unit comprise a database with thresholds for tests. The laboratory control unit can determine if a test result is outside of the threshold of a normal test result by comparing the test result with the stored threshold of the given test.

If the test result is outside of the threshold of a normal test result, the test result may be flagged as a patient critical information. In case the test result is a time sensitive information or an information that may have an imminent effect on the patient's health and well-being, the test result is flagged, by the control unit, as Urgent, and displayed with highest priority to the lab operator. The test result may be transferred automatically via LIS to the clinician and displayed as Urgent test result to recommend taking immediate action.

In one embodiment, the laboratory control unit may receive, from a physician, information specifying particular patient critical results which are needed immediately irrespective of pre-defined thresholds. The control unit stores the information specifying particular patient critical results obtained from the physician and maps all results obtained for the selected patient with the information specifying particular patient critical results. In case a result maps to the stored information specifying particular patient critical results, the result is flagged and immediately displayed to the physician.

The computer-implemented method further comprises prioritizing the display of the patient critical information based on the urgency of the patient critical information. Urgency can be based on how quickly the laboratory operators should be aware of the patient critical information, e.g., time sensitive information, and/or how critical the patient critical information is to the patient's health and well-being. In one embodiment, the display can be prioritized by displaying the patient critical information in order of urgency. For example, the most urgent patient critical information can be displayed at the top of the list of patient critical information and the least urgent at the bottom of the list.

The determination whether a patient critical information is more critical than another patient critical information may be based on information stored in the laboratory control unit, e.g. information on the location of the patient (in the ICU or not), or information on pre-existing test results already indicating an imminent risk. Furthermore, the system may obtain such demographic information which could be used for interpretation ad determination of the level of criticality. Another example for flagging criticality is e.g. if a patient is pregnant. For example, if a patient has a severe heart condition some marker would be considered more critical than compared with a "normal" patient; Another example would be a pregnant woman with high blood pressure would have probably have some critical data to be sorted first due to possible pre eclampsia issues.

In some embodiments, the urgency of the patient critical information can be determined/prioritized by laboratory typology, type of patient test sample, type of patient demographics, and/or combinations thereof.

The extracted patient critical information to be displayed to the laboratory operator can comprise both patient critical notifications and patient critical errors.

Patient critical notifications can comprise patient notifications related to time lapses of the patient test samples (i.e., the patient test samples have expired before the patient test samples have been tested), system alarms, laboratory instrument alarms, laboratory instrument masking, i.e., the turning off of or the stoppage of accepting of test samples to/from a particular laboratory instrument, and combinations thereof.

If the test samples have expired before they have been tested, the patient critical notification would instruct the laboratory operator to obtain a new sample which can be processed by a suitable laboratory source to obtain the required test result.

Another patient critical information could be an alarm of a laboratory source for which calibration is, or a quality control needs to be performed, needed before it can process the test. If necessary, the laboratory control unit would repeat the processing of the sample to obtain the required test result.

Patient critical errors can comprise patient notifications related to patient test sample errors, quality control errors, laboratory instrument alarms, laboratory hardware alarms, and combinations thereof.

The computer-implemented method can further comprise the execution of laboratory actions remotely by the laboratory operator, i.e., when the laboratory operator is not physically present in the laboratory. Such laboratory actions can be, for example, the resolution of a patient critical error that is the source of the display of the patient critical information entry on the display dashboard.

In one embodiment, the laboratory control unit requests login information from a memory which keeps updated login information from the login, authentication and certification process of the laboratory or hospital. Thus, the laboratory control unit is connected to such memory. The login information specifies the device on which the laboratory operator or physician is logged in. The laboratory control unit may also receive preregistered active time-frames of the laboratory operator or physician. Based on this information, the laboratory control unit identifies a device dashboard to which alerts are sent.

This permits the laboratory operator or physician to receive alerts on patient critical information and to take the necessary actions.

In one specific embodiment, the laboratory control unit monitors if the alert was resolved. The alert may be resolved by the laboratory operator or physician confirming on the dashboard that the action required by the alert was taken. If the laboratory control unit does not detect a resolution of the alert, it will send the alert to additional laboratory operators or physicians who are determined to be logged in with the same permissions as the first laboratory operator or physician.

In one embodiment, the display dashboard displaying the patient critical information to the laboratory operator can be on an output display such as, for example, a monitor of a laboratory device or a monitor of a dedicated laboratory system computer, that is physically located within the laboratory.

In one embodiment, the display dashboard displaying the patient critical information to the laboratory operator can be on an output display that situated remotely from the laboratory, i.e., not physically located within the laboratory, such as, for example, a portable computing device of the laboratory operator or a personal computer of the laboratory operator located outside of the laboratory.

According to a second aspect of the present disclosure, a laboratory system for consolidating and prioritizing critical information for a patient in a laboratory is presented. The laboratory system can comprise a plurality of laboratory sources in the laboratory and a laboratory database both comprising patient critical information about a specific patient from a population of patients associated with the laboratory. The laboratory system can also comprise a laboratory control unit communicatively connected to the plurality of laboratory sources and to the laboratory database and configured to extract the patient critical information about the specific patient from the plurality of laboratory sources and the laboratory database. The laboratory system can also comprise a dashboard display communicatively connected to the laboratory control unit and configured to receive the extracted patient critical information about the specific patient from the laboratory control unit and to display the extracted patient critical information about the specific patient to a laboratory operator on a single dashboard display in order of patient critical information urgency.

A non-transitory computer-readable medium storing instructions thereon which when executed by a computer processor controls a computer system to perform the steps of the above method is also presented.

An advantage of the present disclosure is that the computer-implemented method and laboratory system allow for the consolidation and prioritization of already existing patient result related notifications from many different laboratory sources and databases to one single display dashboard in order to notify the laboratory operator quickly and efficiently of any patient workflow blockages/errors and/or critical patient workflow results. Thus, a laboratory operator will be presented with a patient centric system designed to collect all the data focused on a specific patient on one display dashboard so that the laboratory operator can be notified and address (or flag) only the situations that have an impact on that specific patient.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 3 illustrates an exemplary display of the consolidated and prioritized critical information for a patient according to an embodiment of the present disclosure.

DETAILED DESCRIPTION

Figure 1:
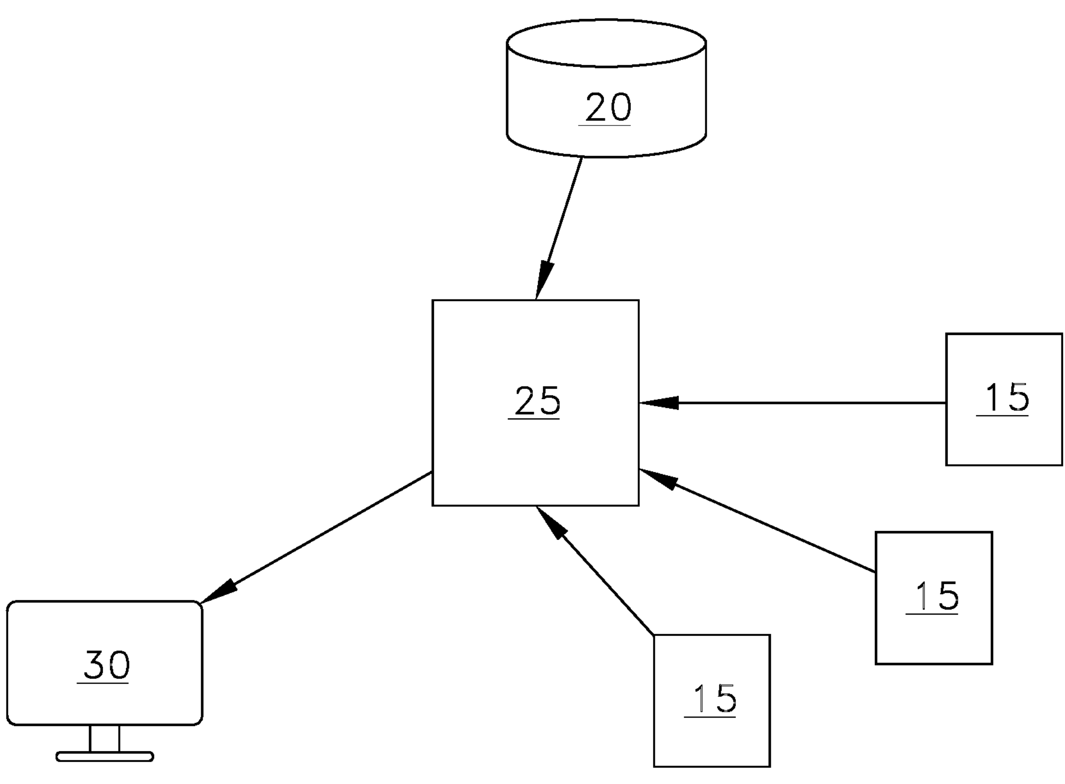
FIG. 1 illustrates a laboratory system of consolidating and prioritizing critical information for a patient according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

The use of the 'a' or 'an' can be employed to describe elements and components of the embodiments herein. This is done merely for convenience and to give a general sense of the inventive concepts. This description should be read to include one or at least one and the singular The term 'laboratory middleware' as used in the present description can refer to any physical or virtual processing device configurable to control a laboratory instrument/device or system comprising one or more laboratory instruments/devices in a way that workflow(s) and workflow step(s) can be conducted by the laboratory instrument/system. The laboratory middleware may, for example, instruct the laboratory instrument/system to conduct pre-analytical, post analytical and analytical workflow(s)/workflow step(s). The laboratory middleware may receive information from a data management unit regarding which steps need to be performed with a certain test sample. In some embodiments, the laboratory middleware can be integral with a data management unit, can be comprised by a server computer and/or be part of one laboratory instrument/device or even distributed across multiple instruments/devices of the laboratory automation system. The laboratory middleware may, for instance, be embodied as a programmable logic controller running a computer-readable program provided with instructions to perform operations.

The term "control unit" or "workflow control unit", as used herein can be a broad term and can be given its ordinary and customary meaning to a person of ordinary skill in the art and may not be limited to a special or customized meaning. The term specifically may refer, without limitation, to an electronic device configured, specifically, by hardware and/or by software programming, for controlling the functionality of the sample processing system within the laboratory middleware. The workflow control unit may further be configured for data exchange with the at least one monitoring system and/or at least one cloud server. Specifically, the workflow control unit may be or may comprise a computing device within the laboratory middleware, such as at least one processor, configured for receiving an electronic signal, such as the at least one item of information, from the at least one monitoring system and/or the at least one cloud server, and for further evaluating the received signal. Further, the workflow control unit may be configured for controlling the functionality based on the received and evaluated signal, for example, based on the at least one item of information.

A 'data storage unit' or 'database' can be a computing unit for storing and managing data such as a memory, hard disk or cloud storage. This may involve data relating to biological/medical test sample(s) to be processed by the automated system. The data management unit may be connected to an LIS (laboratory information system) and/or an HIS (hospital information system). The data management unit can be a unit within or co-located with a laboratory instrument/device. It may be part of the laboratory middleware. Alternatively, the database may be a unit remotely located. For instance, it may be embodied in a computer connected via a communication network.

The present disclosure provides a system and methodology to efficiently consolidate and prioritize hierarchically patient information in such a way that the patient critical information always appears first to the laboratory operator.

Referring initially to FIG. 1, FIG. 1 illustrates a laboratory system of consolidating and prioritizing critical information for a patient. The laboratory system 10 comprises a plurality of laboratory sources 15 in the laboratory and a laboratory database 20. Both the plurality of laboratory sources 15 and the laboratory database 20 comprise patient critical information about a specific patient from a population of patients associated with the laboratory. In one embodiment, the plurality of laboratory sources 15 can comprise, for example, HCA, laboratory databases, monitoring and validation processes, and/or ICA. In another embodiment, the plurality of laboratory sources can be, for example, laboratory devices or instruments such as, for example, pre-analytic devices, analytical devices, and/or post-analytical devices, laboratory middleware, and/or a laboratory information system (LIS)/hospital information system (HIS). The laboratory database 20 can comprise patient data that may or may not be displayed to the laboratory operator.

The laboratory system 10 also comprises a laboratory control unit 25 communicatively connected to the plurality of laboratory sources 15 and to the laboratory database 20 and configured to extract the patient critical information about the specific patient from the plurality of laboratory sources 15 and the laboratory database 20.

The laboratory system 10 also comprises a dashboard display 30 communicatively connected to the laboratory control unit 25 configured to receive the extracted patient critical information about the specific patient from the laboratory control unit 25. The dashboard display 30 is configured to display the patient critical information about the specific patient extracted from the plurality of laboratory sources 15 and the laboratory database 20 to a laboratory operator on a single dashboard display 30 in order of the urgency of the patient critical information. In one embodiment, the dashboard display 30 can be graphic user interface (GUI) displayed on a laboratory monitor within the laboratory or, in another embodiment, the dashboard display 30 can be displayed on a personal computing device of the laboratory operator such as, for example, a smartphone, tablet, laptop computer, and/or on a desktop computer of the laboratory operator.

Figure 2:
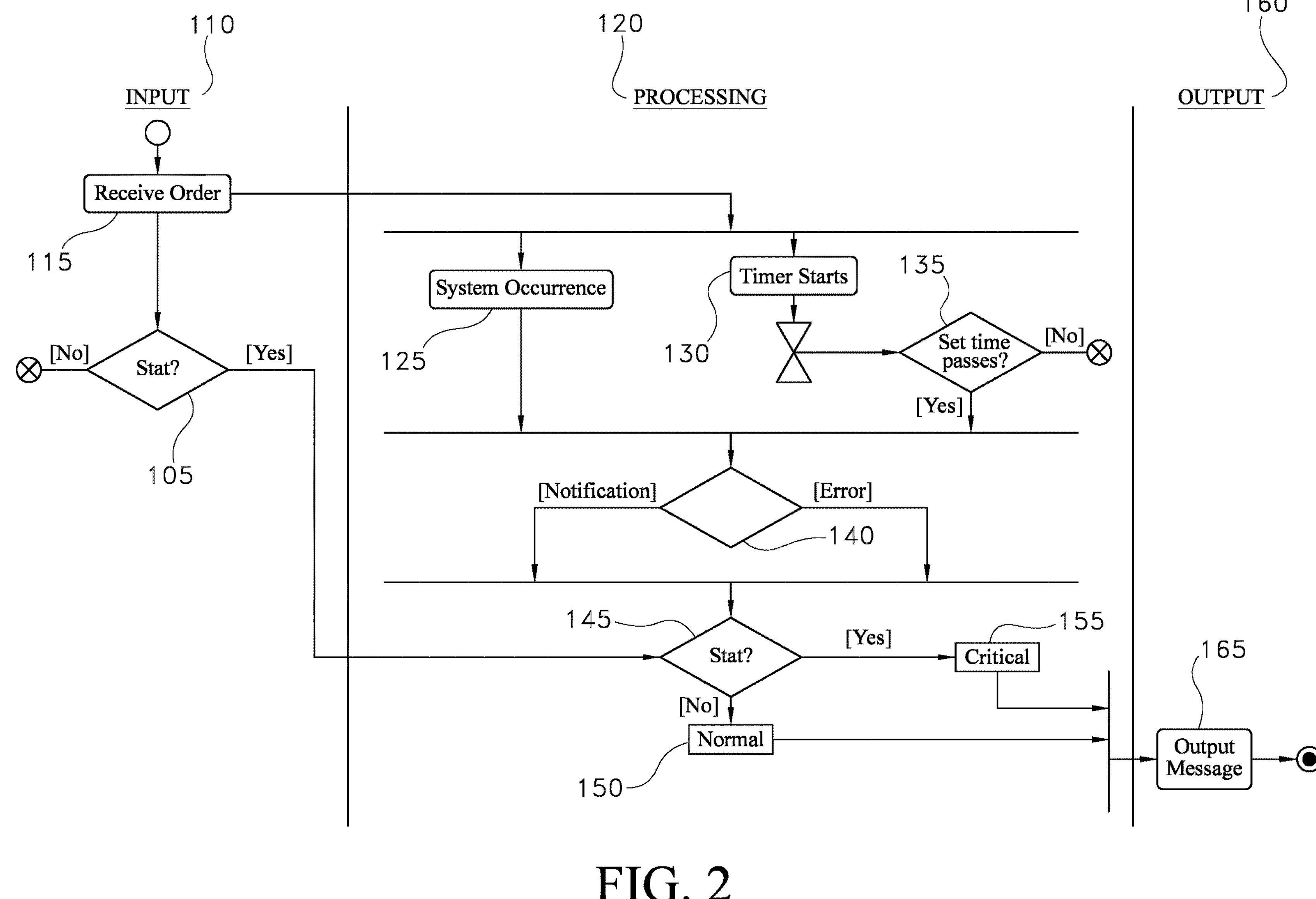
FIG. 2 illustrates a flowchart of the computer-implemented method of consolidating and prioritizing critical information for a patient according to an embodiment of the present disclosure.

Turning to FIG. 2, FIG. 2 illustrates a flowchart of the computer-implemented method of consolidating and prioritizing critical information for a patient on a display dashboard. In the first step of the method 105, a patient from a population of patients associated with the laboratory is selected to be monitored for critical information regarding that patient and input 110 is received concerning that patient. In one embodiment, the received input can be a patient order 115 from a HIS/LIS via the laboratory control unit. Additionally, in step 105, the computer-implemented method can determine whether to start 105 the process of consolidating and prioritizing the patient critical information for the laboratory operator.

If it is determined that the process should be started in step 105, the processing 120 begins to extract information about the patient from a plurality of laboratory sources in the laboratory. The plurality of laboratory sources can comprise, for example, HCA, laboratory databases, monitoring and validation processes, and/or ICA. The patient information can comprise, for example, laboratory workflow event information 125 that could compromise the test results of the patient such as, for example, when the patient critical information is interfering with laboratory workflow or patient critical test results.

The patient critical information could also comprise determining if a preset time for the testing of the test sample of the patient has elapsed 135. In one embodiment, the preset time can be the time that has elapsed once the patient test sample has been placed in the laboratory and a timer was started 130. For example, the preset time can represent the acceptable amount of time that the patient test sample may be used for testing before the patient test sample expires and can no longer be used.

The patient information that is extracted can then be sorted into notification information and error information in step 140. Once the patient information has been sorted, it can then be determined by the control unit, in step 145, if the patient information is normal 150 or if the patient information is patient critical 155.

Patient critical errors can comprise, for example, notifications regarding patient test sample errors, quality control errors, instrument alarms, laboratory hardware alarms, and combinations thereof. Patient critical notifications can comprise, for example, notifications regarding time lapses of the patient test samples, alarms, instrument alarms, instrument masking, and combinations thereof.

Once the patient information is determined to be either normal 150 or patient critical 155, the patient information can be sent to be outputted/displayed 160 onto a dashboard display. In one embodiment, the control unit can also sort the extracted patient critical information based on the urgency of the extracted patient critical information, e.g., the most urgent patient critical information can be displayed to the laboratory operator first.

In step 165, all of the patient critical information 155 can then be displayed on a single display dashboard to a laboratory operator. In one embodiment, the outputted display dashboard can be displayed to the laboratory operator in the laboratory on, for example, a laboratory monitor and/or a personal computing device of the laboratory operator. In another embodiment, the outputted display dashboard can be displayed remotely to the laboratory operator outside of the laboratory on a personal computing device such as, for example, a smartphone, tablet, laptop, and/or a desktop computer.

Finally, turning to FIG. 3, FIG. 3 illustrates an exemplary laboratory display dashboard of the consolidated and prioritized critical information for a patient. In one embodiment, the laboratory display dashboard 200 provides the patient critical information on the one display dashboard, in a series of columns. For example, in column 210, the laboratory workflow steps in which a patient critical occurrence happened are listed. In one embodiment, the steps, in column 210, can be prioritized, or ranked, for example, in order of urgency to the patient. The ranking of the steps can be based, for example, according to laboratory typology, type of laboratory test sample, patient demographics, and/or combinations thereof. In column 215, the type of patient critical information associated with the workflow step is provided.

In column 220, the patient critical information is prioritized/graded as either normal or critical/STAT. The grading column 220 can be further divided into the type of patient critical information that is being displayed. The type of information could be a notification (column 225) or an error (column 227). As described above, patient critical errors can comprises, for example, notifications regarding patient test sample errors, quality control errors, instrument alarms, laboratory hardware alarms, and combinations thereof and patient critical notifications can comprises, for example, notifications regarding time lapses of the patient test samples, alarms, instrument alarms, instrument masking, and combinations thereof. Finally, in column 230, an explanation of the patient critical information is provided to the laboratory operator.

In one embodiment, a laboratory operator can execute procedures to act on/resolve the consolidated and prioritized patient critical information directly on the display dashboard 200 with a user input device such as, for example, a stylus, mouse, keyboard, touch screen, and the like. The laboratory operator can execute the procedures when s/he is physically in the laboratory or s/he can be in a setting remote from the laboratory.

For example if there was some sort of degradation of sample integrity for an urgent sample, data relating to sample integrity is received by the laboratory control unit during preanalytic analysis and a critical notification is sent for an additional phlebotomy to be performed.

Another example is if an analytical instrument goes offline or has a processing error. If a patient critical test is to be performed on that said instrument, the lab technician would be notified to take appropriate actions such as basic troubleshooting, processing on another instrument, sending the sample to another lab or contacting an engineer to repair said instrument.

Further disclosed and proposed is a computer program product including computer-executable instructions for performing the disclosed method in one or more of the embodiments enclosed herein when the program is executed on a computer or computer network. Specifically, the computer program may be stored on a computer-readable data carrier or a server computer. Thus, specifically, one, more than one or even all of method steps as indicated above may be performed by using a computer or a computer network, preferably by using a computer program.

As used herein, a computer program product refers to the program as a tradable product. The product may generally exist in any format, such as in a paper format, or on a computer-readable data carrier on premise or located at a remote location. Specifically, the computer program product may be distributed over a data network (such as a cloud environment). Furthermore, not only the computer program product, but also the execution hardware may be located on premise or in a cloud environment.

Further disclosed and proposed is a computer-readable medium comprising instructions which, when executed by a computer system, cause a laboratory automation system to perform the method according to one or more of the embodiments disclosed herein.

Further disclosed and proposed is a modulated data signal comprising instructions, which, when executed by a computer system, cause a laboratory automation system to perform the method according to one or more of the embodiments disclosed herein.

Referring to the computer-implemented aspects of the disclosed method, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

The invention claimed is:

1. A computer-implemented method of consolidating and prioritizing critical information for a patient in a laboratory, the method comprising:

selecting a patient to monitor from a population of patients associated with the laboratory, wherein at least one sample from said patient was requested to be processed by a laboratory source comprised in said laboratory;

extracting information for the patient from a plurality of laboratory sources in the laboratory by a laboratory control unit, wherein the laboratory control unit is communicatively connected to the plurality of laboratory sources, wherein said information for the patient comprises a test result obtained from processing said sample, and/or additional information relating to critical;

determining by the laboratory control unit if the extracted patient information is critical to care of the patient, wherein said determining comprises determining if the test result indicates that the sample, laboratory source or test comprised errors, or if the test result was within or outside a normal test result range or determining, from the additional information relating to critical care, that the extracted patient information is critical to care of the patient;

wherein said extracted patient critical information is determined as critical to care if a test result is urgently required for life-saving treatment of the patient; and in response to determining that the extracted patient information is critical to care of the patient, automatically outputting the extracted patient critical information by the laboratory control unit to a single display dashboard for display to a laboratory operator or a physician; and automatically sorting the extracted patient critical information on the single display dashboard according to a determined level of criticality of the extracted patient critical information;

receiving laboratory workflow event information from the laboratory control unit when the patient critical information is impeding laboratory workflow; and automatically displaying the laboratory workflow event information on the single display dashboard along with the extracted patient critical information.

2. The computer-implemented method of claim 1, wherein said laboratory control unit determines that a test result is urgently needed if the test result indicates that the patient is in a critical situation, or information relating to the patient received by the laboratory control unit indicates that the patient is in a critical situation; and in response to determining that the test result is urgently needed, outputting an alert.

3. The computer-implemented method according to claim 1, wherein the patient critical information is extracted by the laboratory control unit from a laboratory database, wherein the laboratory control unit is communicatively connected to the laboratory database.

4. The computer-implemented method according to claim 1, further comprising:

in response to determining that the patient critical information is interfering with the laboratory workflow, transmitting laboratory workflow event information from the laboratory control unit and displaying the transmitted laboratory workflow event information along with the extracted patient critical information on the display dashboard.

5. The computer-implemented method according to claim 1, further comprising, prioritizing the display of the patient critical information based on an urgency of the patient critical information.

6. The computer-implemented method according to claim 5, wherein the urgency of the patient critical information is based on laboratory typology, type of sample, type of patient demographics, and/or combinations thereof.

7. The computer-implemented method according to claim 1, wherein the extracted patient critical information comprises patient critical notifications and patient critical errors.

8. The computer-implemented method according to claim 7, wherein patient critical errors comprises notifications regarding sample errors, quality control errors, instrument alarms, laboratory hardware alarms, and/or combinations thereof.

9. The computer-implemented method according to claim 7, wherein patient critical notifications comprises notifications regarding time lapses, alarms, instrument alarms, instrument masking, and/or combinations thereof.

10. The computer-implemented method according to claim 1, further comprising, executing actions remotely to resolve a patient critical error that is a source of the display of the patient critical information entry on the display dashboard.

11. The computer-implemented method according to claim 1, wherein the outputted display dashboard is displayed in the laboratory to the laboratory operator.

12. The computer-implemented method according to claim 1, wherein the outputted display dashboard is displayed remotely to the laboratory operator outside of the laboratory.

13. A non-transitory computer-readable medium storing instructions thereon which when executed by a computer processor controls a computer system to perform any one of the methods according to claim 1.

14. The computer-implemented method according to claim 1, wherein the laboratory control unit extracts error information from the workflow event information related to the patient and determines at least one corrective action to be taken based on the error information.

15. The computer-implemented method according to claim 14, wherein the at least one corrective action is displayed on the single display dashboard along with the extracted patient critical information.

16. The computer implemented method according to claim 15, wherein the laboratory workflow event information, the extracted patient critical information, and the at least one corrective action are all automatically sorted on the single display dashboard according to a determined urgency or a determined criticality.

17. A laboratory system for consolidating and prioritizing critical information for a patient in a laboratory, the laboratory system comprising:

a plurality of laboratory sources comprising patient critical information about a specific patient from a population of patients associated with the laboratory;

a laboratory database comprising patient critical information about a specific patient from a population of patients associated with the laboratory;

a laboratory control unit communicatively connected to the plurality of laboratory sources and to the laboratory database and configured to extract the patient critical information about the specific patient from the plurality of laboratory sources and the laboratory database; and a dashboard display communicatively connected to the laboratory control unit and configured to receive the extracted patient critical information about the specific patient from the laboratory control unit and to automatically display the extracted patient critical information about the specific patient to a laboratory operator on a single dashboard display in order of patient critical information urgency, wherein the extracted patient critical information is automatically sorted and displayed according to a determined level of criticality of the extracted patient critical information, wherein the dashboard display receives laboratory workflow event information from the laboratory control unit when the patient critical information is impeding laboratory workflow; and wherein the dashboard display automatically displays the laboratory workflow event information on the single display dashboard along with the extracted patient critical information.

18. The laboratory system of claim 17 wherein said laboratory control unit is configured to:

determine that a test result is urgently needed if the test result indicates that the patient is in a critical situation, or information relating to the patient received by the laboratory control unit indicates that the patient is in a critical situation; and in response to determining that the test result is urgently needed, outputting an alert.

19. The laboratory system of claim 17 wherein said laboratory control unit is configured to:

in response to determining that the patient critical information is interfering with laboratory workflow, causing the laboratory workflow event information along with the extracted patient critical information to be displayed on the display dashboard.

20. The laboratory system of claim 17 wherein said laboratory control unit is configured to:

in response to determining that a laboratory workflow event comprises a patient critical result, causing information regarding the laboratory workflow event along with the extracted patient critical information to be displayed on the display dashboard.

21. The laboratory system of claim 17 wherein the laboratory unit is configured to cause the dashboard display to display the patient critical information based on a prioritizing of the urgency of the patient critical information.

22. The laboratory system of claim 17 wherein the urgency of the patient critical information is based on laboratory typology, type of sample, type of patient demographics, and/or combinations thereof.

* * * * *